United States Patent [19]
Vounatsos

[11] Patent Number: 5,531,693
[45] Date of Patent: Jul. 2, 1996

[54] SINGLE-USE SYRINGE

[76] Inventor: Constantin Vounatsos, 19, rue des Bois, 78490 Galluis, France

[21] Appl. No.: 343,538
[22] PCT Filed: Apr. 9, 1993
[86] PCT No.: PCT/FR93/00362
§ 371 Date: Nov. 29, 1994
§ 102(e) Date: Nov. 29, 1994
[87] PCT Pub. No.: WO93/20873
PCT Pub. Date: Oct. 28, 1993

[30] Foreign Application Priority Data

Apr. 10, 1992 [FR] France .................................. 92 04384

[51] Int. Cl.⁶ .................................................. A61M 5/00
[52] U.S. Cl. ........................................... 604/110; 604/228
[58] Field of Search ............................. 604/110, 187, 604/218, 263, 195, 228

[56] References Cited

U.S. PATENT DOCUMENTS

| | | |
|---|---|---|
| 4,731,068 | 3/1988 | Hesse . |
| 4,863,427 | 9/1989 | Cocchi . |
| 4,915,692 | 4/1990 | Verlier .................................... 604/110 |
| 4,931,043 | 6/1990 | Ray et al. ............................... 604/228 |
| 4,932,941 | 6/1990 | Min et al. . |
| 4,950,243 | 8/1990 | Estruch ............................... 604/218 X |
| 5,045,063 | 9/1991 | Spielberg .............................. 604/110 |
| 5,125,899 | 6/1992 | Frignoli ................................ 604/110 |
| 5,135,495 | 8/1992 | Arcusin ................................ 604/110 |

FOREIGN PATENT DOCUMENTS

| | | |
|---|---|---|
| 0392228 | 10/1990 | European Pat. Off. . |
| 0409134 | 1/1991 | European Pat. Off. . |
| 2653668 | 5/1991 | France . |
| 2015883 | 9/1979 | United Kingdom . |
| 2202747 | 10/1988 | United Kingdom . |

Primary Examiner—John D. Yasko
Attorney, Agent, or Firm—Pollock, Vande Sande & Priddy

[57] ABSTRACT

Device for rendering a syringe unusable after a first injection, wherein the plunger head is disconnected from the body of the plunger, and the plunger head is left permanently in the body of the syringe.

7 Claims, 3 Drawing Sheets

SINGLE-USE SYRINGE

The present invention relates to a device for rendering a syringe unusable after a first injection. The syringes as manufactured at present can be reused after a first injection and for this reason are vehicles transmitting and spreading various diseases.

The device according to the invention makes it possible to rectify this disadvantage; according to a first characteristic, it in fact has the ability to leave the head of the plunger permanently in the body of the syringe after a first injection, the said head of the plunger being disconnected from the body of the plunger when an attempt is made to pull the plunger back after a first injection.

According to particular embodiments:

The body of the syringe can comprise, in the inner part which receives the plunger, two areas of extra thickness which will result in changes in internal diameter at these points. One will be situated near the outlet for the liquid to be injected, the other near the inlet of the body of the syringe.

The object of the first area of extra thickness will be to act as a non-return stop for retaining the head of the plunger and causing the disconnection of the head of the plunger from the body of the plunger when the latter is pulled back after a first injection. The second area of extra thickness prevents the assembly of plunger head and plunger body from being withdrawn from the body of the syringe, prior to a first injection, for tampering with the disconnection device.

The plunger can consist of a body and of a head. These two parts will be connected via a system comprising a slotted cylindrical cavity on the plunger head, and a truncated cylinder on the body of the plunger. The truncated part of the cylinder prevents the cylinder from being re-engaged in the slotted cylindrical cavity of the head of the plunger when the assembly has been disconnected a first time.

Alternatively, the connection system can consist of a slotted trapezoidal cavity on the plunger head, and of a male trapezoid on the plunger body.

The attached drawings illustrate the invention:

Figure 1:
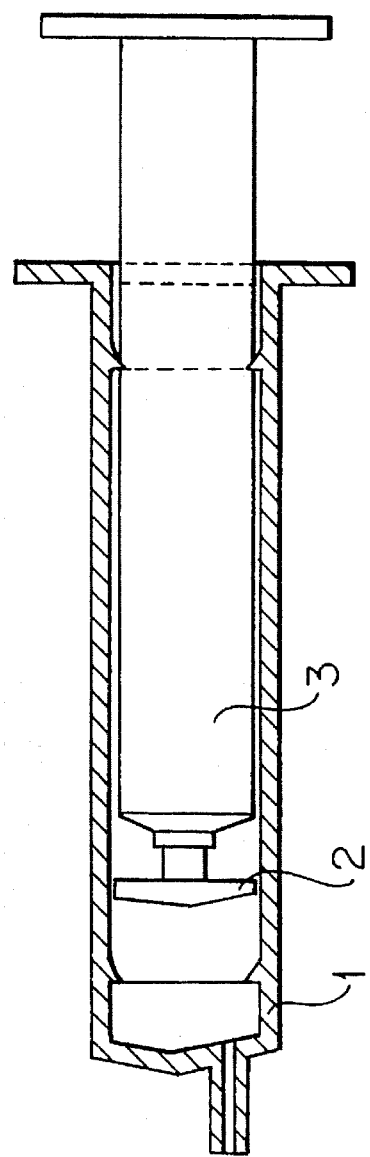
FIG. 1 shows, in section, the device according to the invention.
Figure 2:
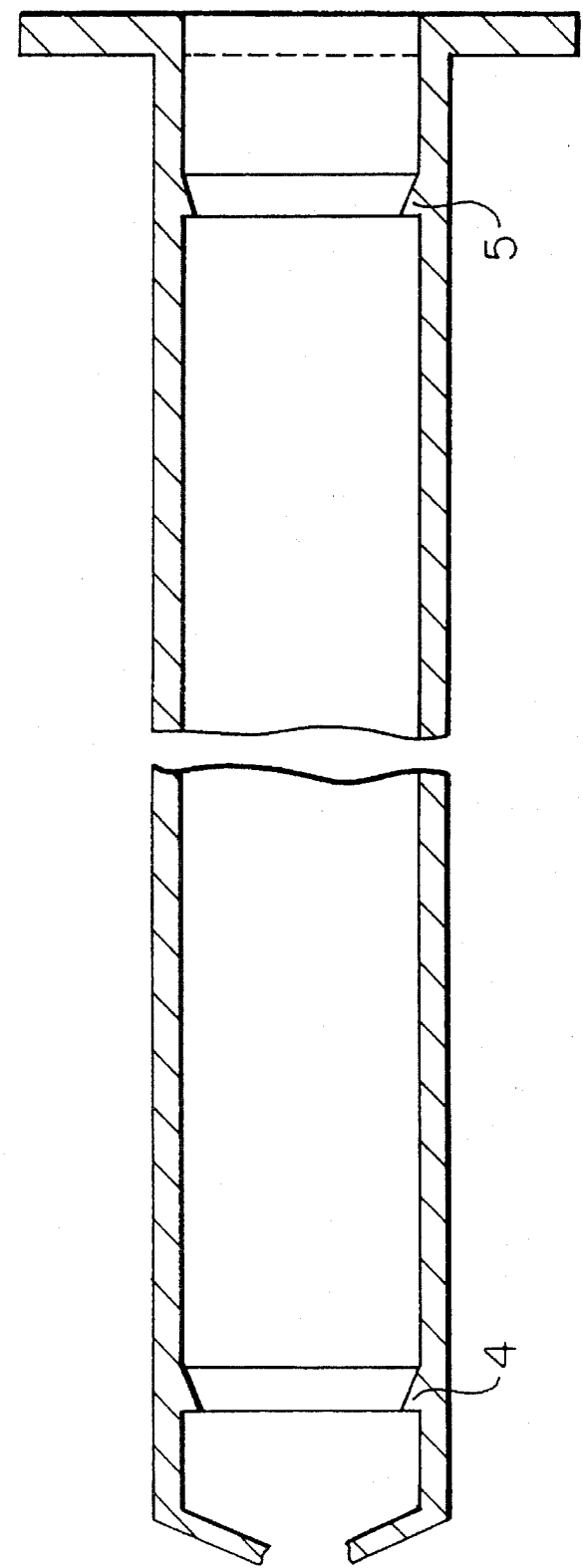
FIG. 2 shows, in section, the feature changing the diameter of the body of the syringe according to the invention.
Figure 3B:
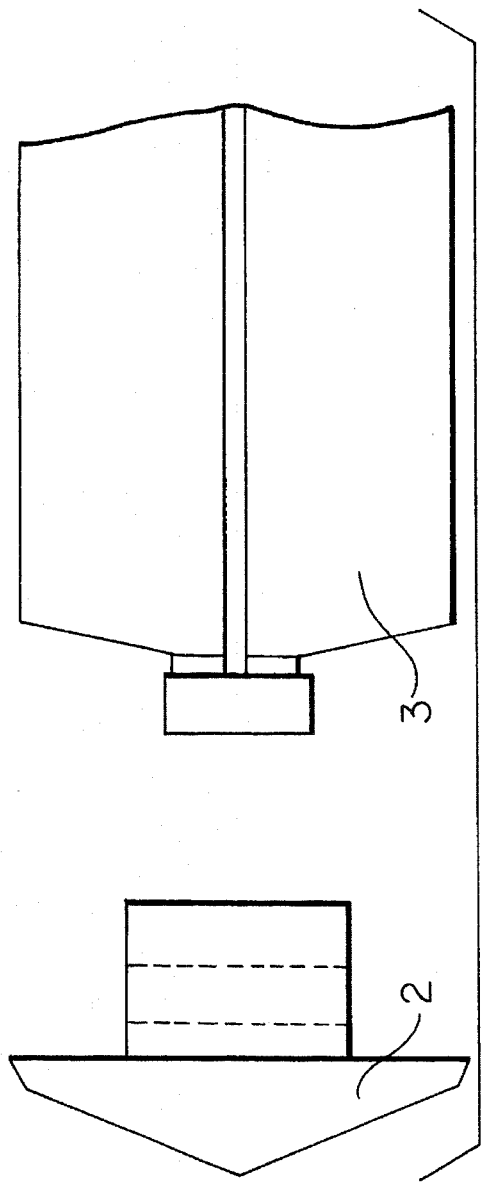
FIG. 3 shows the connection between the plunger head and the body of the plunger according to the invention.
Figure 3C:
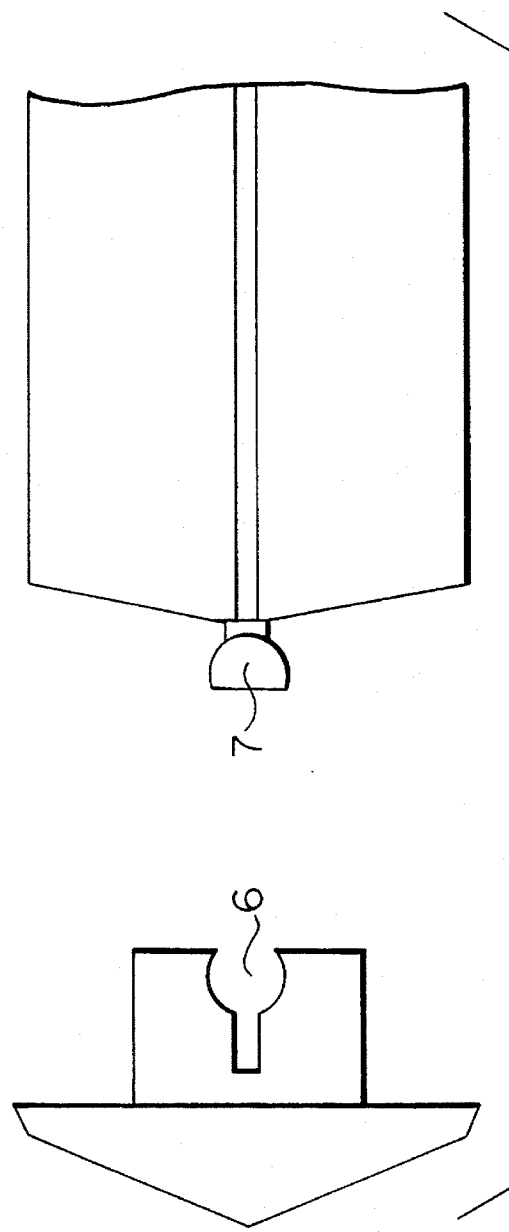
Figure 3A:
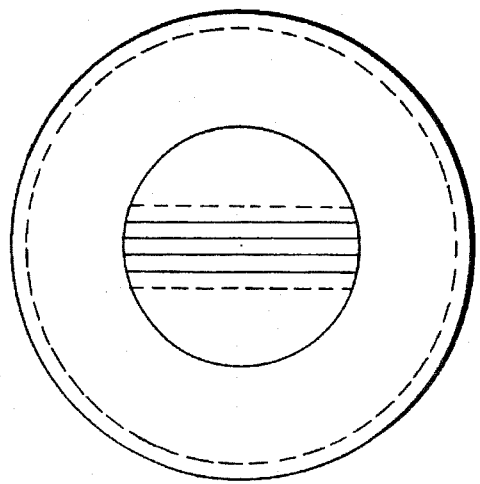
Figure 4C:
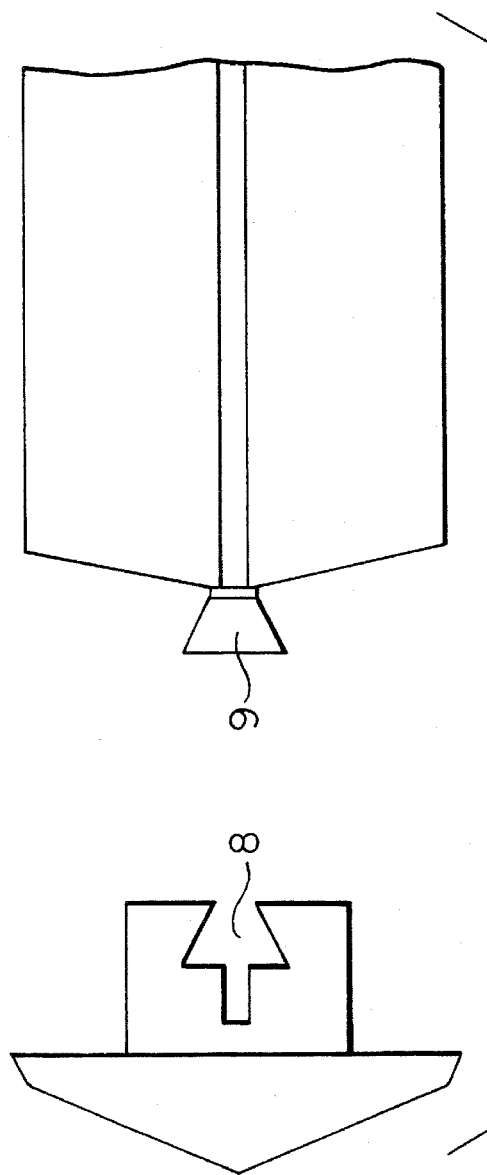
FIG. 4 shows the alternative connection between the plunger head and the body of the plunger according to the invention.
Figure 4B:
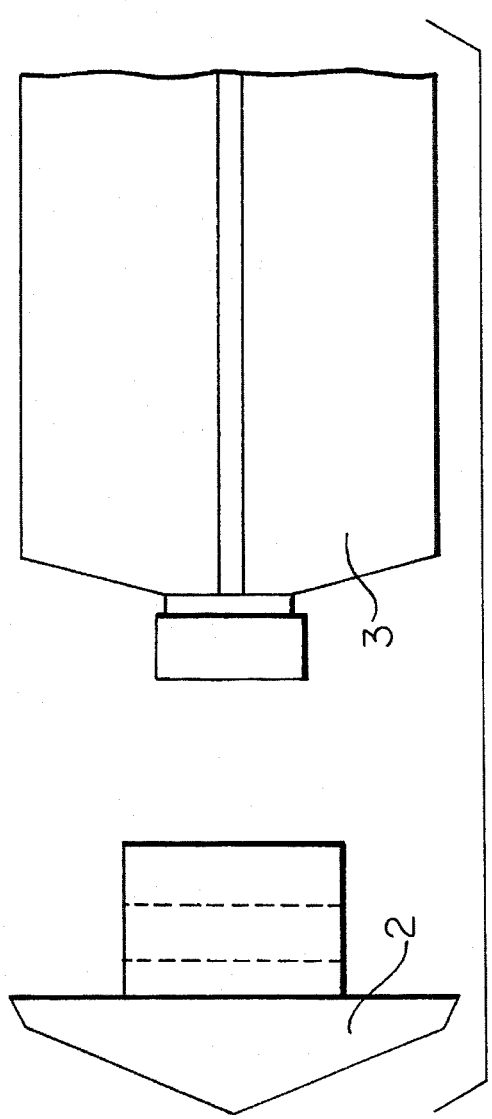
Figure 4A:
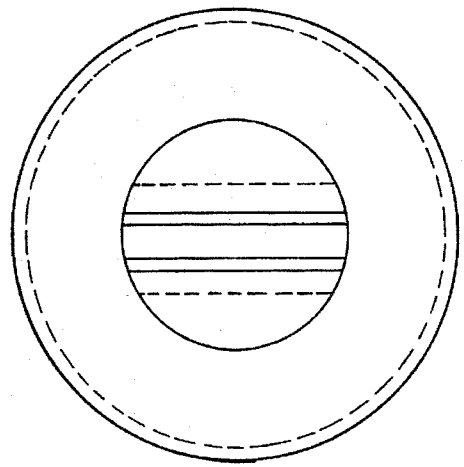

With reference to these drawings, the device comprises a syringe body (1) designed so as to create two rings of extra thickness (4) and (5) serving as non-return stops in the inner cylinder.

The plunger head (2), which is designed to fit perfectly in the syringe body, comprises, at its base, an assembly consisting of a female cavity which is cylindrical (6) or (alternatively) trapezoidal (8) and is slotted in order to permit elasticity.

The plunger 2, having an external diameter which is slightly smaller than the internal diameter of the body of the syringe, ends with a male component which is cylindrical (7) or alternatively trapezoidal (9).

The device according to the invention is intended to render the syringe unusable after a first injection. Given that the resistance of the stop is greater than the resistance of the connection, when an attempt is made to pull the plunger back, the two components, namely the plunger head and the body of the plunger, are disconnected and prohibit permanently the reuse of the syringe.

I claim:

1. A single-use syringe comprising:

a syringe body;

a plunger enclosed and slidable within the syringe body, the plunger including
   a) a head serving as a piston and located within the syringe body;
   b) an elongated rod-like body for actuating movement of the syringe head;
   c) an intermediate stem directly connected between the head and the plunger body;
   d) a slotted cavity formed in the stem for receiving a mating projection on a confronting surface of the elongated body, to form a releasable connection therebetween, disconnection occurring in response to attempted withdrawal of the plunger;

a first continuous annular raised stop transversely formed on an interior wall of the syringe body, at a first end of the syringe, to resist plunger head withdrawal in response to attempted retraction, after full insertion of the plunger head into the syringe body; and a second continuous annular raised stop transversely formed on an interior wall of the syringe body, at a second end of the syringe, to resist plunger head withdrawal beyond the second stop, in response to retraction of the plunger head beyond the first stop.

2. Device according to claim 1, wherein the slotted cavity is cylindrical.

3. Device according to claim 1, wherein the projection is a truncated cylinder that prevents reassembly after a first disconnection.

4. Device according to claim 1, wherein the slotted cavity is trapezoidal.

5. Device according to claim 1, wherein the projection trapezoidal.

6. Device according to claim 4, wherein the projection is trapezoidal.

7. Device according to claim 2, wherein the projection is a truncated cylinder.

* * * * *